(12) United States Patent
Okawa

(10) Patent No.: US 8,747,305 B2
(45) Date of Patent: Jun. 10, 2014

(54) ENDOSCOPE SYSTEM AND ENDOSCOPIC OBSERVATION METHOD

(75) Inventor: Atsushi Okawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 1861 days.

(21) Appl. No.: 11/805,754

(22) Filed: May 24, 2007

(65) Prior Publication Data

US 2007/0276184 A1 Nov. 29, 2007

(30) Foreign Application Priority Data

May 29, 2006 (JP) .................................. 2006-148039

(51) Int. Cl.
*A61B 1/06* (2006.01)
(52) U.S. Cl.
USPC ........................................................ 600/170
(58) Field of Classification Search
CPC ........... A61B 1/00009; A61B 1/00096; A61B 1/00163; A61B 1/00177
USPC .......................................... 600/109, 117, 170
See application file for complete search history.

(56) References Cited

U.S. PATENT DOCUMENTS

| 6,035,229 | A  | * | 3/2000 | Silverstein et al. | 600/473 |
| 7,801,584 | B2 | * | 9/2010 | Iddan et al. | 600/407 |
| 2003/0117491 | A1 | * | 6/2003 | Avni et al. | 348/77 |
| 2004/0073087 | A1 | * | 4/2004 | Glukhovsky et al. | 600/109 |
| 2004/0220478 | A1 | * | 11/2004 | Wallace et al. | 600/476 |
| 2004/0249247 | A1 | * | 12/2004 | Iddan | 600/170 |
| 2005/0250991 | A1 | * | 11/2005 | Mizuno | 600/160 |
| 2006/0195014 | A1 | * | 8/2006 | Seibel et al. | 600/102 |

FOREIGN PATENT DOCUMENTS

| JP | 55-116330 | | 9/1980 |
| JP | 4-36644 | A | 2/1992 |
| JP | 6-304127 | A | 11/1994 |
| JP | 2001-029313 | A | 2/2001 |
| JP | 2004-105725 | | 4/2004 |
| JP | 2004-535878 | A | 12/2004 |
| JP | 2005-143668 | A | 6/2005 |
| JP | 2005-319315 | A | 11/2005 |

* cited by examiner

*Primary Examiner* — Philip R Smith
(74) *Attorney, Agent, or Firm* — Scully, Scott, Murphy & Presser, P.C.

(57) ABSTRACT

To provide an endoscope system that includes a light source, an insertion part to be inserted into a living organism for guiding a illumination light emitted from the light source and a light returned from the living organism, a deflection optical system for outwardly directing the illumination light in a radius direction of the insertion part and for introducing a light inwardly returned from the living organism in the radius direction into the insertion part, a part for capturing the returned light, a part for detecting an insertion speed of the insertion part, a part for adjusting a frame rate for the image capturing of the image capturing part based on the detected insertion speed, an image forming part for arranging acquired images at a pitch based on the insertion speed to form an image of the inside of the living organism, and a part for displaying the formed image.

6 Claims, 11 Drawing Sheets

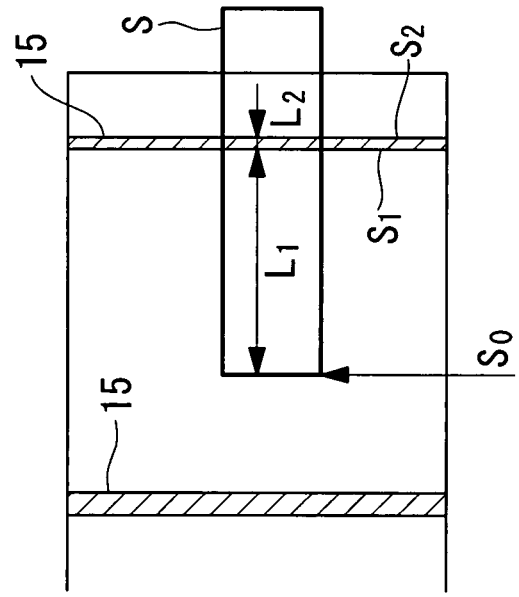

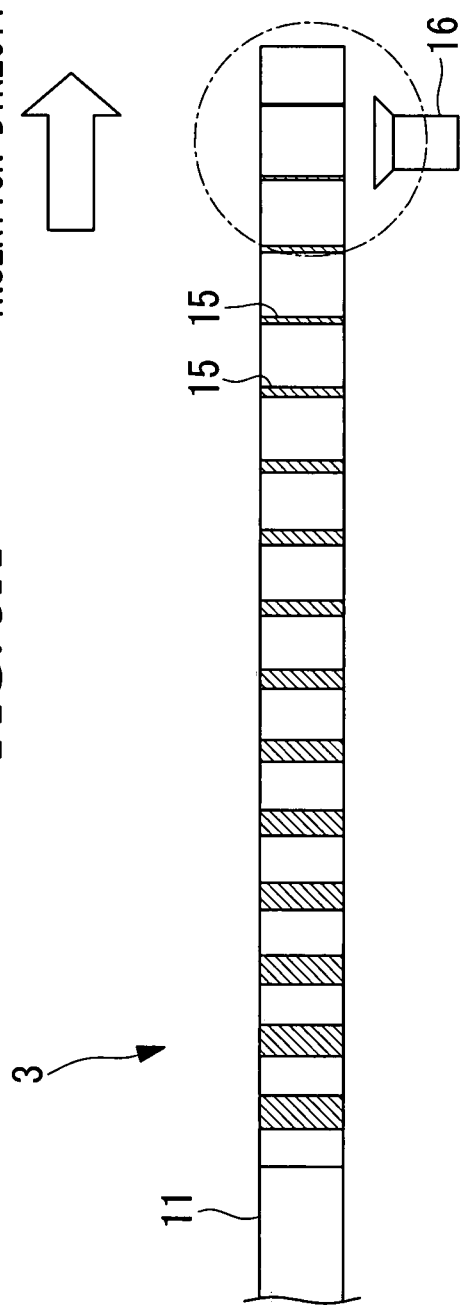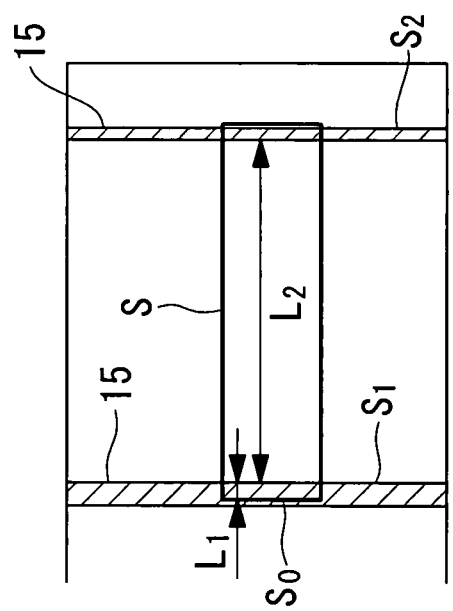

ENDOSCOPE SYSTEM AND ENDOSCOPIC OBSERVATION METHOD

BACKGROUND OF THE INVENTION

1. Field of the Invention

The present invention relates to an endoscope system and an endoscopic observation method. This application is based on Japanese Patent Application No. 2006-148039, the content of which is incorporated herein by reference.

2. Description of Related Art

In an conventional endoscope system, in order to correctly detect a location of a tip of an insertion part to be inserted into a body cavity of a living organism, a mark that indicates a distance from the tip of the insertion part is provided on an outer surface of the insertion part, and the mark is read using a reading device. The technique is disclosed, for example, in Japanese Unexamined Patent Application Publication No. 55-116330 and Japanese Unexamined Patent Application Publication No. 2004-105725.

In the case of a side view observation that acquires images of an subject in a direction orthogonal to an insertion direction, because an outer diameter of the insertion part is limited, the image to be acquired at one acquisition is a strip-shaped image that has a very narrow width along the insertion direction of the insertion part. Then, to acquire sequential images in the insertion direction of the insertion part within a desired range, it is necessary to repeat the image capturing by sending the each image by the width of the strip-shaped image acquired at one acquisition.

However, generally, the insertion part of the endoscope is manually inserted into the living organism by an operator. Then, the amount of the image to be transmitted and the insertion speed are not constant. Accordingly, if the insertion part is quickly inserted, the acquired images become fragments, and the image of the affected part may not be acquired.

BRIEF SUMMARY OF THE INVENTION

The present invention provides the following solutions. According to an aspect of the invention, an endoscope system includes a light source for emitting an illumination light to illuminate an living organism, an insertion part to be inserted into the living organism for guiding the illumination light emitted from the light source and a light returned from the living organism, a deflection optical system being provided at a tip of the insertion part for outwardly directing the illumination light guided through the insertion part in a direction of a radius of the insertion part and for introducing a light inwardly returned from the living organism in the direction of the radius of the insertion part into the insertion part, an image capturing part for capturing the returned light guided through the insertion part, an insertion speed detection part for detecting an insertion speed of the insertion part, a frame rate adjustment part for adjusting a frame rate for the image capturing of the image capturing part based on the insertion speed detected by the insertion speed detection part, an image forming part for arranging strip-shaped images acquired by the image capturing part at a pitch based on the insertion speed to form an image of the inside of the living organism, and, a display part for displaying the image formed by the image forming part.

In the above aspect of the present invention, it is preferable that the endoscope system includes an exposure correction part that corrects an exposure time of the image capturing part based on the insertion speed detected by the insertion speed detection part, and a sensitivity correction part that corrects a sensitivity of the image capturing part based on the exposure time corrected by the exposure correction part.

In the above aspect of the present invention, the insertion speed detection part may include a mark being provided on an outer surface of the insertion part along an insertion direction, a mark detection part for detecting the mark, and a speed calculation part for calculating an insertion speed based on the detected mark.

In the above aspect of the present invention, the returned light may include at least one of a fluorescence and a white light. In the above aspect of the present invention, the deflection optical system may include a conical mirror.

According to an another aspect of the invention, an endoscopic observation method in which an illumination light is outwardly emitted from a tip of an insertion part to be inserted into a living organism in a radius direction at each position in an insertion direction, a light returned from the living organism is captured to acquire strip-shaped images, the acquired images are arranged to form an image of the inside of the living organism, and the formed image is displayed, the method includes detecting an insertion speed of the insertion part, and adjusting a frame rate for acquiring the strip-shaped images based on the detected insertion speed. In the aspect of the present invention, it is preferable that an exposure time for acquiring the strip-shaped images is corrected based on the detected insertion speed and a sensitivity is corrected based on the corrected exposure time.

BRIEF DESCRIPTION OF THE SEVERAL VIEWS OF THE DRAWINGS

FIG. 2A and FIG. 2B are views illustrating a speed detection part of an insertion part in the endoscope system of FIG. 1;

FIG. 3A and FIG. 3B are views illustrating a speed detection part similar to that of FIG. 2A and FIG. 2B;

DETAILED DESCRIPTION OF THE INVENTION

Figure 1:
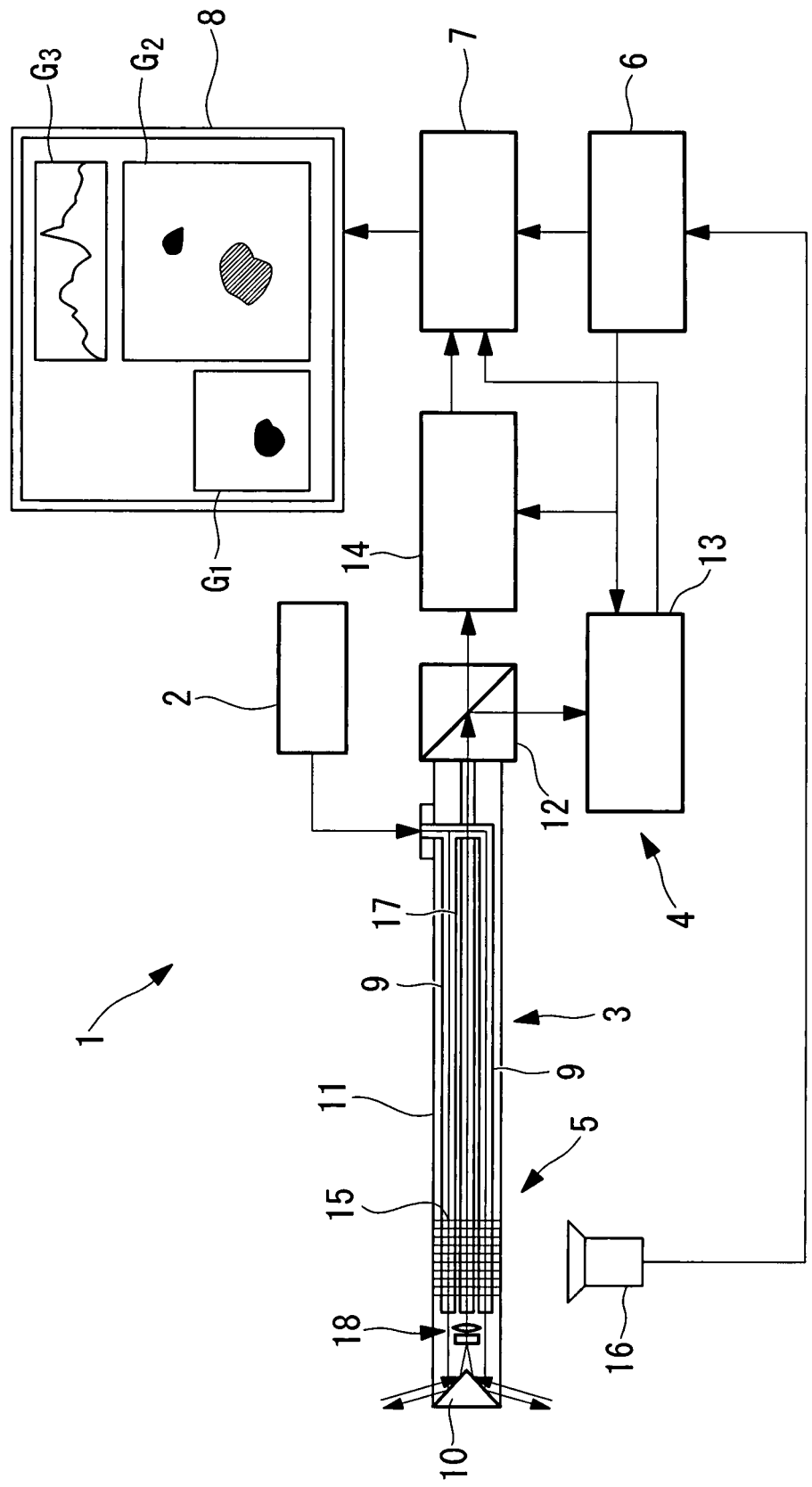
FIG. 1 is a schematic structural view illustrating an endoscope system according to an embodiment of the present invention.

An endoscope system 1 according to a first embodiment of the present invention is described with reference to FIGS. 1 to 11. An endoscopic observation apparatus 1 according to the embodiment includes, as shown in FIG. 1, a light source 2, an elongated insertion part 3 that is connected to the light source 2 and to be inserted into a body cavity, a light detection part (image capturing part) 4 that is connected to the insertion part 3 and detects a returned light that is returned from a living organism, i.e., a subject, a speed detection part (insertion speed detection part) 5 that detects a moving speed of the insertion part 3, a control part (frame rate adjustment part, exposure correction part, sensitivity correction part, speed calculation part) 6 that controls the light detection part 4 based on the moving speed detected by the speed detection part 5, an image processing part (image forming part) 7 that forms an image of the living organism based on the image information detected by the light detection part 4 and the moving speed detected by the speed detection part 5, and an image display part (display part) 8 that displays the image of the living organism created by the image processing part 7.

As the light source 2, for example, a xenon lamp or a halogen lamp that emits a wide-spectrum light such as a white light or an excitation light is employed. The insertion part 3 includes a light guide (or an optical fiber bundle) 9, a conical mirror (deflection optical system) 10, an image guide 17, an image-forming optical system 18, and an outer tube 11. The light guide 9 guides the light emitted from the light source 2 to a tip of the insertion part 3. The conical mirror 10 is disposed at the tip of the insertion part 3 and deflects the light transmitted in the light guide 9 outwardly and radially in a radius direction and introduces a returned light inwardly heading from the living organism in the direction of the radius of the insertion part 3 into the insertion part 3. The image guide 17 guides the returned light introduced by the conical mirror 10 to a back end side of the insertion part 3. The image-forming optical system 18 is disposed between the conical mirror 10 and the image guide 17, and forms the image of the living organism on the top end surface of the image guide 17. The outer tube 11 covers the light guide 9. At the back end of the insertion part 3, a dichroic prism 12 is provided that splits lights into a white light which is reflected at the living organism and returned and a fluorescence generated when a fluorescent material in the living organism is excited.

The light detection part 4 includes a white light detector (image capturing part) 13 that detects the white light split by the dichroic prism 12 and a fluorescence detector (image capturing part) 14 that detects the split fluorescence. The speed detection part 5 includes a plurality of marks 15 that are provided on an outer surface of the outer tube 11 with spaces in a longitudinal direction and an image sensor (mark detection part) 16 that captures the marks 15.

With respect to the marks 15 that are provided on the outer tube 11, for example, as shown in FIGS. 2A, 2B, 3A and 3B, the strip-shaped marks 15 can be provided at a certain intervals in the insertion direction and have different widths. As shown in FIGS. 2A, 2B, 3A and 3B, an insertion direction of the insertion part 3 can be detected using a reference position $S_0$ which is a left end of a rectangular target area S of the image sensor 16, on the basis of a distance $L_1$ between the reference position $S_0$ and an edge $S_1$ of the mark 15 that is a nearest mark from the reference position $S_0$, and a distance $L_2$ between the edge $S_1$ and an edge $S_2$ that is adjacent to the edge $S_1$.

For example, as shown in FIG. 2A and FIG. 2B, in the case where only a single mark 15 is disposed within the target area S of the image sensor 16, a moving distance of the insertion part 3 can be calculated based on the distance $L_1$ between the reference position $S_0$ in the target area S and the left side edge $S_1$ that is the nearest mark from the reference position $S_0$, and the width $L_2$ of the mark 15. The width $L_2$ of the mark 15 is unique to each mark 15. Accordingly, the distance from the tip of the insertion part 3 to the mark 15 is known. Then, the moving distance of the insertion part 3 can be calculated by obtaining the distance $L_1$ from the edge $S_1$ of the mark 15 to the reference position $S_0$ of the image sensor 16.

For example, as shown in FIG. 3A and FIG. 3B, in the case where only two marks 15 are disposed within the target area S of the image sensor 16, a moving distance of the insertion part 3 can be calculated based on the distance $L_1$ between the reference position $S_0$ in the target area S and the right side edge $S_1$ that is the nearest mark from the reference position $S_0$, and the width $L_2$ that is a space between the two marks 15. The space width $L_2$ of the two marks 15 is unique to the marks 15. Accordingly, the distance from the tip of the insertion part 3 to the mark 15 is known. Then, the moving distance of the insertion part 3 can be calculated by obtaining the distance $L_1$ from the edge $S_1$ of the mark 15 to the reference position $S_0$ of the image sensor 16.

An insertion speed of the insertion part 3 can be calculated by dividing a difference between moving distances that are calculated at two time positions by the time length between the time positions. The control part 6 is adapted to perform the operations of the moving distance and the insertion speed of the insertion part 3 and adjust a frame rate of the white light detector 13 and the fluorescence detector 14 based on the calculated insertion speed. For example, when the insertion speed is increased, the control part 6 adjusts the frame rate to increase, and when the insertion speed is decreased, the control part 6 adjusts the frame rate to decrease.

Figure 4:
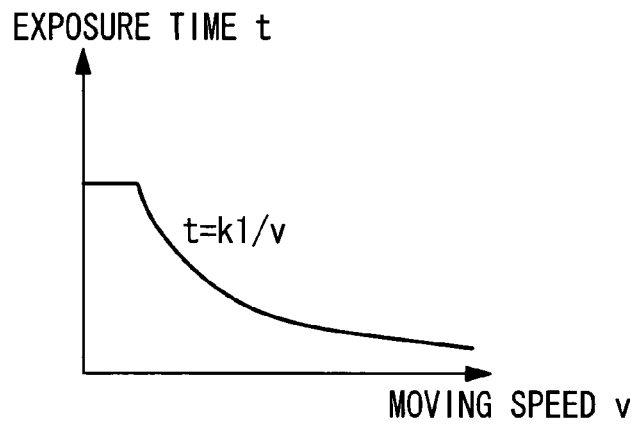
FIG. 4 is a graph illustrating a relationship between a moving speed of the insertion part and an exposure time of a light detector in the endoscope system of FIG. 1.
Figure 5:
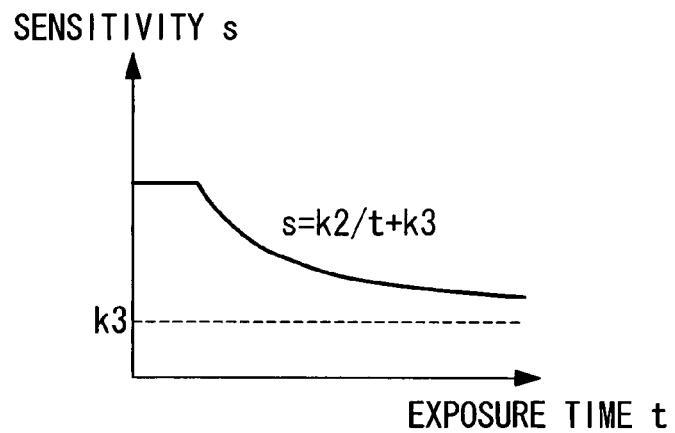
FIG. 5 is a graph illustrating a relationship between the exposure time and a sensitivity of the light detector in the endoscope system of FIG. 1.
Figure 6:
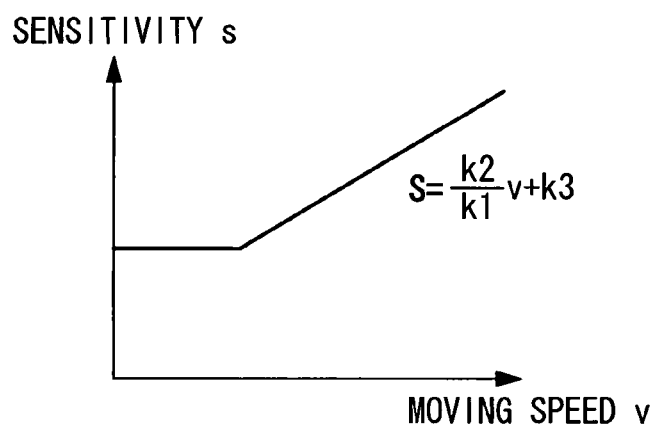
FIG. 6 is a graph illustrating a relationship between the moving speed of the insertion part and the sensitivity of the light detector in the endoscope system of FIG. 1.

The control part 6 is adapted to correct exposure times and sensitivities of the white light detector 13 and the fluorescence detector 14 as the insertion speed of the insertion part 3 is increased. The relationship between the insertion speed v and the exposure time t is shown in FIG. 4. The relationship between the exposure time t and the sensitivities s is shown in FIG. 5. According to the FIGS. 4 and 5, the relationship between the insertion speed v and the sensitivity s is shown in FIG. 6. As shown in the drawings, in the case where the insertion speed v is increased, the control part 6 is adapted to correct the exposure time t to be reduced and the sensitivity s to be increased, and in the case where the insertion speed v is decreased, the control part 6 is adapted to correct the exposure time t to be increased and the sensitivity s to be decreased.

The image processing part 7 is adapted to form a two-dimensional image by arranging strip-shaped images that are acquired by the light detection parts 13 and 14 at each position of the tip of the insertion part 3 at a predetermined pitch. Based on the insertion speed v of the insertion part 3 and the frame rate f that is set based on the insertion speed v, a predetermined number of strip-shaped images are acquired for a unit length in the insertion direction. Then, the acquired images are arranged at the predetermined pitch that is determined based on the insertion speed v and the frame rate f to form the two-dimensional image.

The image display part 8, for example, is adapted to display a two-dimensional white light image G1 that is detected by the white light detector 13 and is processed by the image processing part 7, a two-dimensional fluorescent image G2 that is detected by the fluorescence detector 14 and is processed by the image processing part 7, and a luminance distribution G3 of the fluorescent image G2 along the insertion direction of the insertion part 3.

An operation of thus structured endoscope system 1 according to the embodiment is described below. Using the endoscope system 1 according to the embodiment, to observe a state in a body cavity of a living organism, the insertion part 3 is inserted into the body cavity, a light emitted from the light source 2 is introduced to the tip of the insertion part 3 through the light guide 9, and the light is outwardly deflected in the radius direction by the conical mirror 10 to radially illuminates the subject. A white light that is reflected and returned at an inner wall of the body cavity that is arranged outwardly in the radius direction of the tip of the insertion part 3 and a fluorescence generated by an excitation of a fluorescent material in the inner wall of the body cavity are returned into the image guide 17 through the conical mirror 10 and the image forming optical system 18. Then, the returned lights are transmitted in the image guide 17 and split by the dichroic prism 12. The split lights are detected by the white light detector 13 and the fluorescence detector 14 respectively.

The images that are acquired within exposure times t per one frame of the respective detectors 13 and 14 set by the control part 6 are images that have a strip shape and have a width geometrically determined according to the size of the conical mirror 10. The images are acquired almost circumferentially in a circumferential direction around an axis line of the insertion part 3. Each image is converted into polar coordinates by the conical reflection plane of the conical mirror, and then, the coordinates are converted into plane coordinates in the image processing part 7.

When the insertion part 3 is moved, in response to an operation of the speed detection part 5, based on a detection signal by the image sensor 16, an insertion speed v is calculated in the control part 6. In the control part 6, a frame rate f, an exposure time t, and a sensitivity s are calculated based on the moving speed v, and then, instruction signals are outputted to respective detectors 13 and 14.

Figure 7:
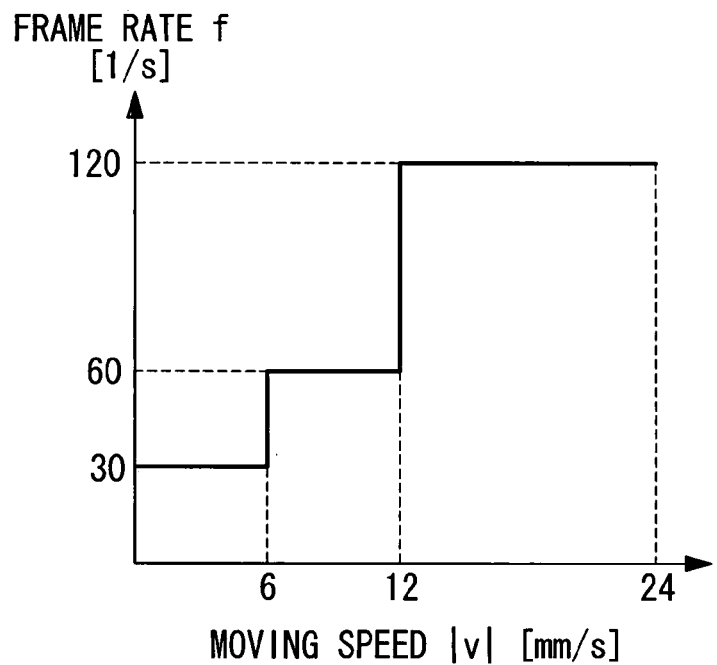
FIG. 7 is a graph illustrating a relationship between the moving speed of the insertion part and a frame rate of the light detector in the endoscope system of FIG. 1.

Here, for example, as shown in FIG. 7, a case that the frame rate f is varied step by step with respect to the moving speed v is described. In the case where a width of a strip-shaped image that is acquired with respect to each one frame is 0.2 mm, for example, if the moving speed v is $0 < v \leq 6$ (mm/s), the frame rate f is set to be f=30 (1/s), if the moving speed v is $6 < v \leq 12$ (mm/s), the frame rate f is set to be f=60 (1/s), and if the moving speed v is $12 < v \leq 24$ (mm/s), the frame rate f is set to be f=120 (1/s). These frame rates f are set such that any space is not formed between the adjacent strip-shaped images in the case where the insertion part 3 is moved at a maximum value within the range of the moving speed v respectively.

Figure 8:
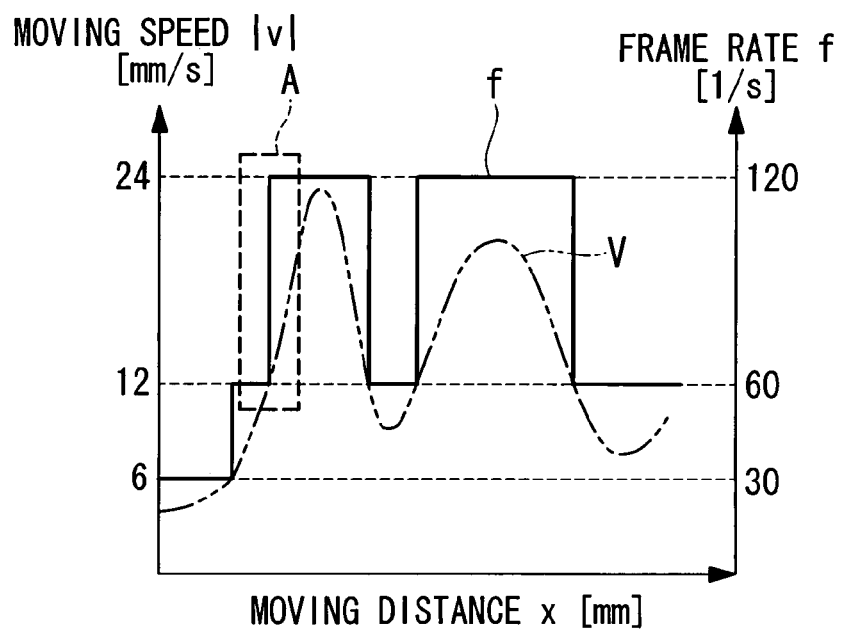
FIG. 8 is a graph illustrating a relationship between a moving distance and the moving speed of the insertion part and the frame rate of the light detector in the endoscope system of FIG. 1.
Figure 9:
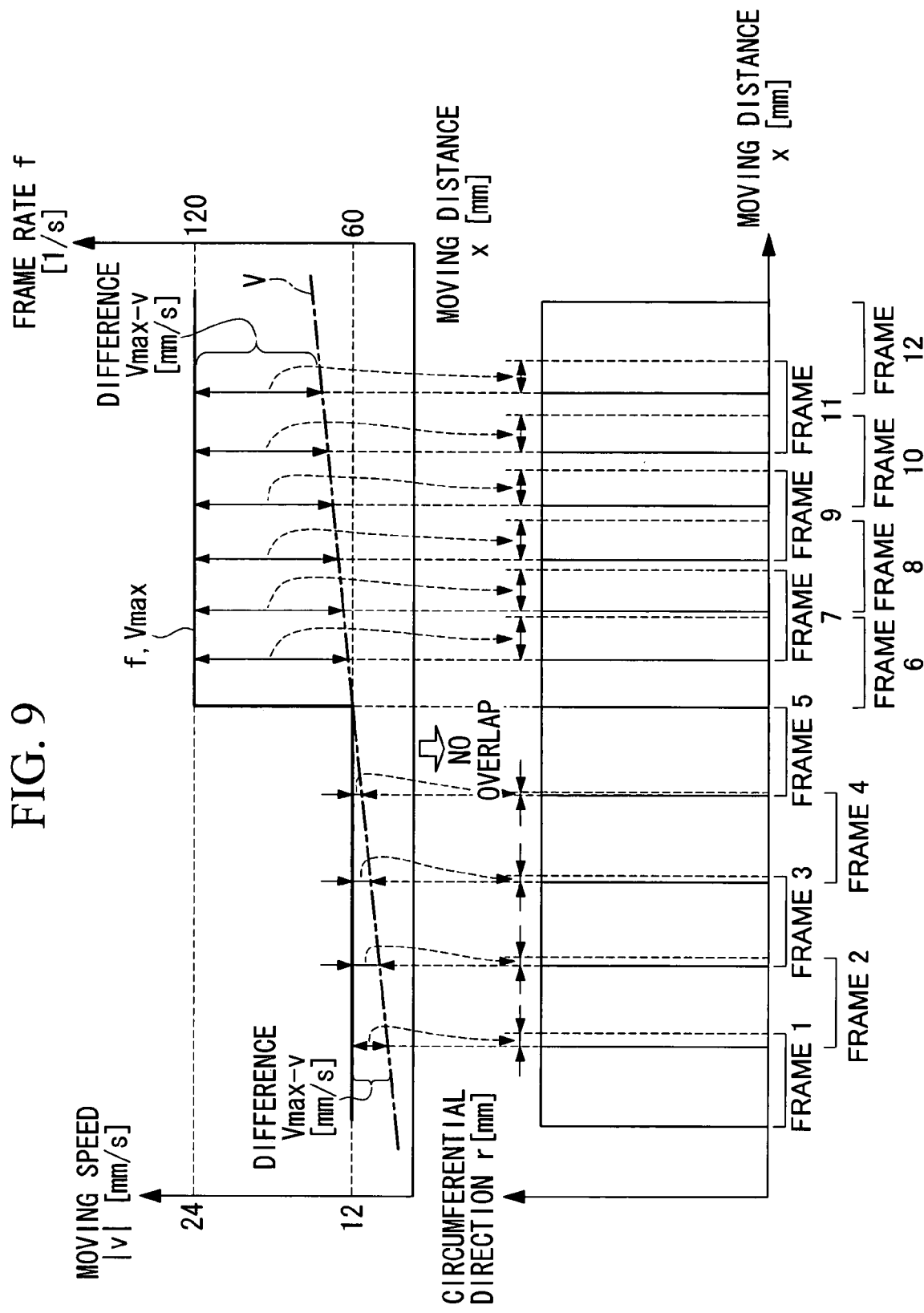
FIG. 9 is a view illustrating detailed data of an A part of FIG. 8 and an exemplary image that is created by arranging strip-shaped images of FIG. 8.

Specifically, as shown by the chained line in FIG. 8, according to the variation of the moving speed v, the frame rate f is varied as shown by the solid line. Then, the acquired strip-shaped images are arranged to correspond to the moving distance of the insertion part 3. Then, as shown in FIG. 9, in the case where the frame rate f is high enough with respect to the moving speed v, the adjacent strip-shaped images are overlapped with each other, and the two-dimensional white light image G1 and the two-dimensional fluorescent image G2 arranged without spaces between the images can be obtained.

Accordingly, the images G1 and G2 formed by the image processing part 7 have no space, and by displaying the images on the image display part 8, the image of the living organism along the insertion direction can be displayed without skips. As a result, it is further ensured that the observer is prevented from overlooking an affected part.

Figure 10:
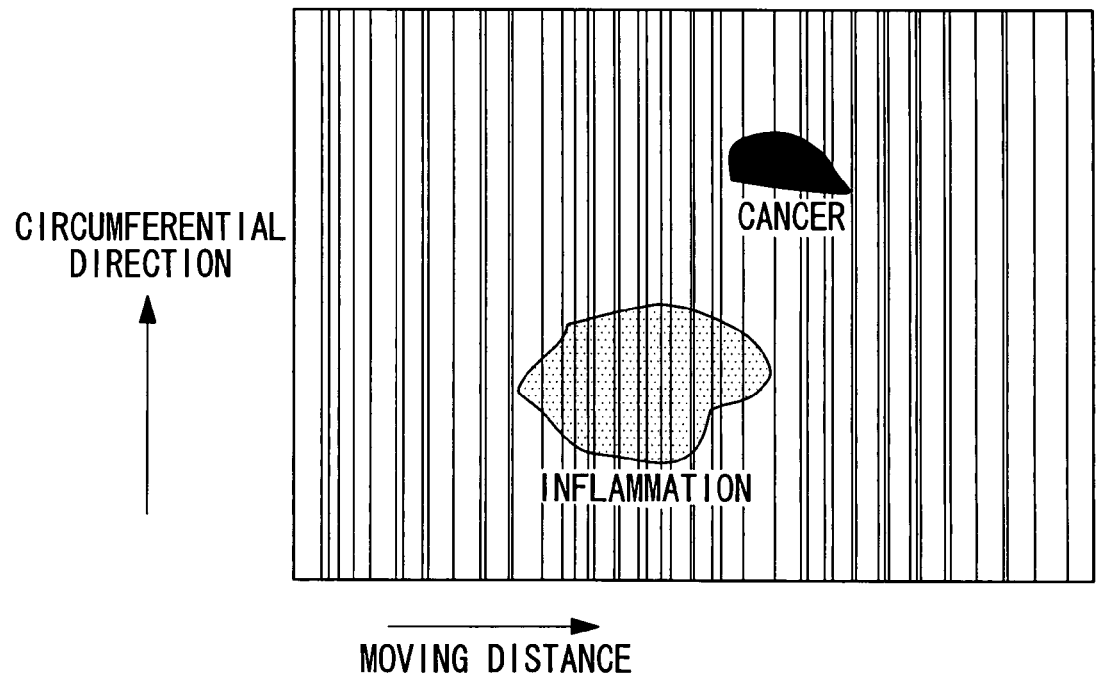
FIG. 10 is a view illustrating an exemplary image that is created using the data of FIG. 9.
Figure 11:
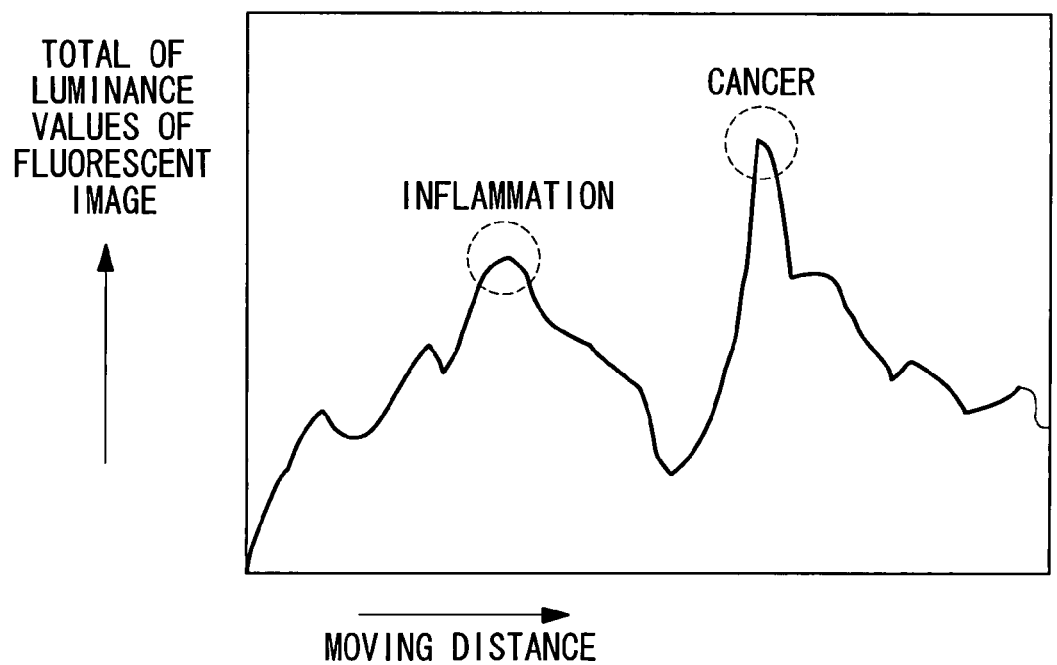
FIG. 11 is a graph illustrating a relationship between the moving distance and a total of luminance values of a fluorescent image in the exemplary image of FIG. 10.

According to the embodiment, even if the moving speed of the insertion part is varied, as shown in FIG. 10, an image that is not distorted in the insertion direction of the insertion part 3 can be obtained. In addition, for example, as shown in FIG. 11, by drawing a graph showing a relationship between a moving distance and a total of fluorescent intensities in a circumferential direction, at a position where a high fluorescent intensity is indicated, an existence of a disease such as a cancer cell or an inflammation can be recognized.

In such a case, according to the embodiment, the exposure time t may be adjusted based on the insertion speed v to shorten the exposure time t in the case where the insertion part 3 is inserted at a fast insertion speed v. Thus, a blurring is reduced. When only the exposure time t is shorten, the intensity of the fluorescent image is varied. However, in the embodiment, the sensitivity s is adjusted corresponding to the exposure time t. Accordingly, the intensity of the fluorescent image is prevented from being varied, and a quantity of the fluorescent image for recognizing the disease can be ensured.

Figure 12:
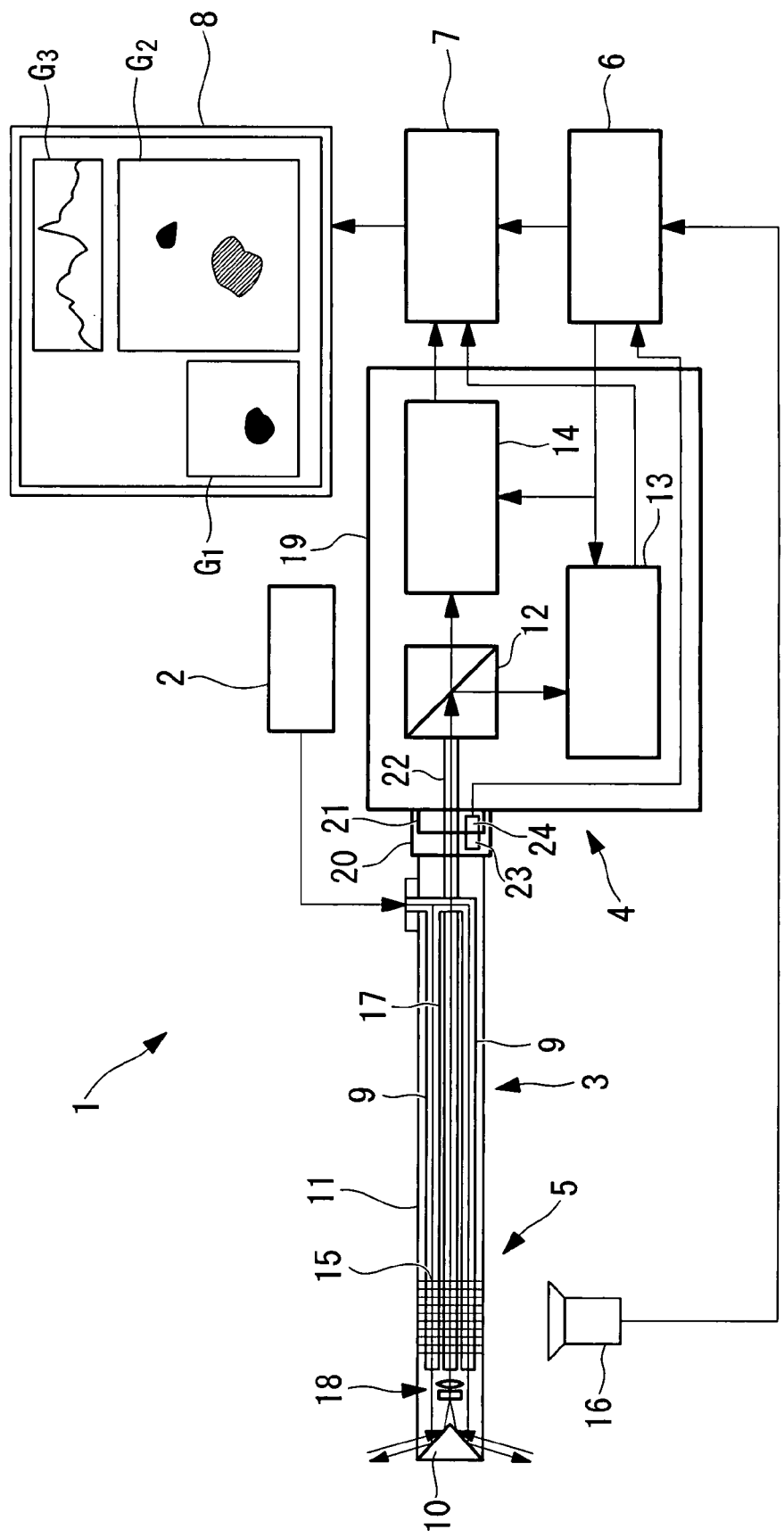
FIG. 12 is a schematic structural view illustrating a modification of the endoscope system of FIG. 1.

In the endoscope system 1 according to the embodiment, as shown in FIG. 12, the insertion part 3 may be structured to be detachable with respect to the white light detector 13 and the fluorescence detector 14. That is, the insertion part 3 may be attached and detached to a light detection device 19 that includes the white light detector 13, the fluorescence detector 14, and the dichroic prism 12 through an optical connector 20.

In such a case, the light detection device 19 includes a receptacle 21 that connects the optical connector 20, a second image guide 22 that connects the receptacle 21 with the dichroic prism 12, and an information detection part 24 that reads information stored in an information storage part 23, which is described below. The optical connector 20 holds the image guide 17 such that the image guide 17 is opposed to an end surface of the second image guide 22 when the optical connector 20 is connected to the receptacle 21, and the optical connector 20 includes the information storage part 23 that is disposed to be opposed to the information detection part 24.

Figure 13:
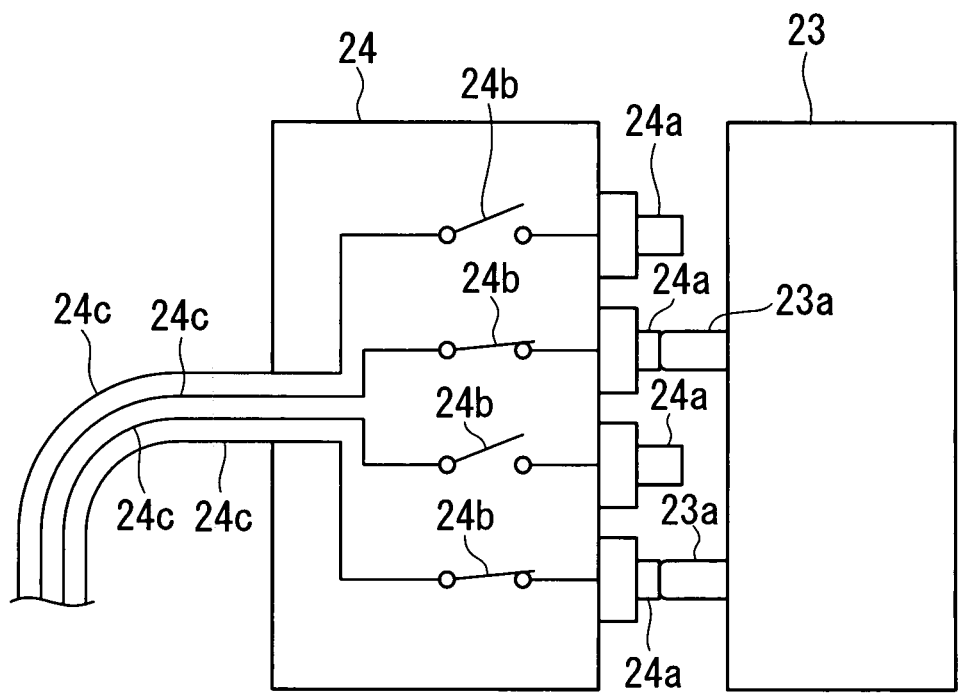
FIG. 13 is a view illustrating an information storage part for storing characteristic information about a deflection optical system and an information detection part for reading the information stored in the information storage part in the endoscope system in FIG. 12.

The information storage part 23 stores information about the width of the strip-shaped image of each one frame that is defined by a shape of the conical mirror 10 disposed at the tip of the insertion part 3. Specifically, the information detection part 24, for example, as shown in FIG. 13, includes a plurality of push pines 24a and switches 24b that are connected to the push pins 24a. The information storage part 23 includes a plurality of detection pins 23a that are disposed at positions corresponding to the positions of a part of the push pins 24a out of the plurality of push pins 24a.

Here, the plurality of detection pins 23a are set such that each insertion part 3 has a different arrangement depending on each width of the strip-shaped image in each one frame defined by the shape of the conical mirror 10. That is, the arrangement of the detection pines 23a stores the information about the width of the strip-shaped image.

The switches 24b are structured to be turned on when the push pins 24a are pushed. That is, only a part of the push pins 24a that are opposed to the detection pins 23a are pushed by the detection pins 23a. Then, only the switches 24b that are being connected to the push pins 24a are selectively electrically conducted.

Thus, the information detection part 24 is adapted to selectively conduct electricity to the part of the plurality of the signal lines 24c, and then, detect the information about the width of the strip-shaped image and output the signal bundle transmitted by the signal lines 24c as a detection signal to the control part 6. In the control part 6, based on the detection signal inputted by the information detection part 24, the width of the strip-shaped image is read, and the setting of the calculation of the frame f corresponding to the moving speed v is changed. Based on the changed setting, the frame rate f, the exposure time t, and the sensitivity s corresponding to the moving speed v are calculated. Then, instruction signals are outputted to the detector 13 and 14 respectively.

In such a case, if the insertion part 3 is replaced, in proportion to the range of the field of view of the conical mirror 10 that is provided at the tip of the insertion part 3, that is, the width of the strip-shaped image in each one frame, the range of the moving speed v is set. For example, in the case where the width of the image is 0.5 mm, if the moving speed v is $0 < v \leq 15$ (mm/s), the frame rate f is set to be f=30 (1/s), if the moving speed v is $15 < v \leq 30$ (mm/s), the frame rate f is set to be f=60 (1/s), and if the moving speed v is $30 < v \leq 60$ (mm/s), the frame rate f is set to be f=120 (1/s). That is, as the width of the image becomes wider, the moving speed can be increased.

With the above structure, according to the change of the width of the strip-shaped image, an appropriate frame rate f can be set. Then, even if the currently used insertion part 3 is replaced with an insertion part 3 that has a different shape in the deflection optical system such as the conical mirror 10, it is possible to obtain a two-dimensional white light image G1 and a fluorescent image G2 that are arranged without spaces between the images. In addition, overlaps of the adjacent strip-shaped images can be reduced to a necessary and minimum value. As a result, the image processing amount can be optimized and it is further ensured that the observer is prevented from overlooking the affected part.

Figure 14:
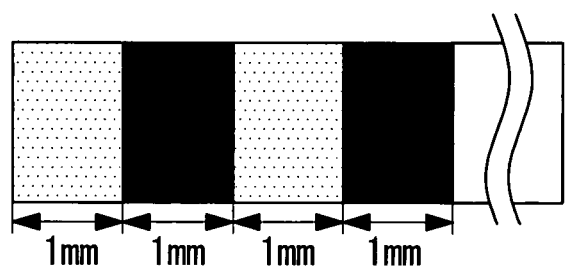
FIG. 14 is a view illustrating a modification of the mark that is provided on the insertion part.
Figure 15:
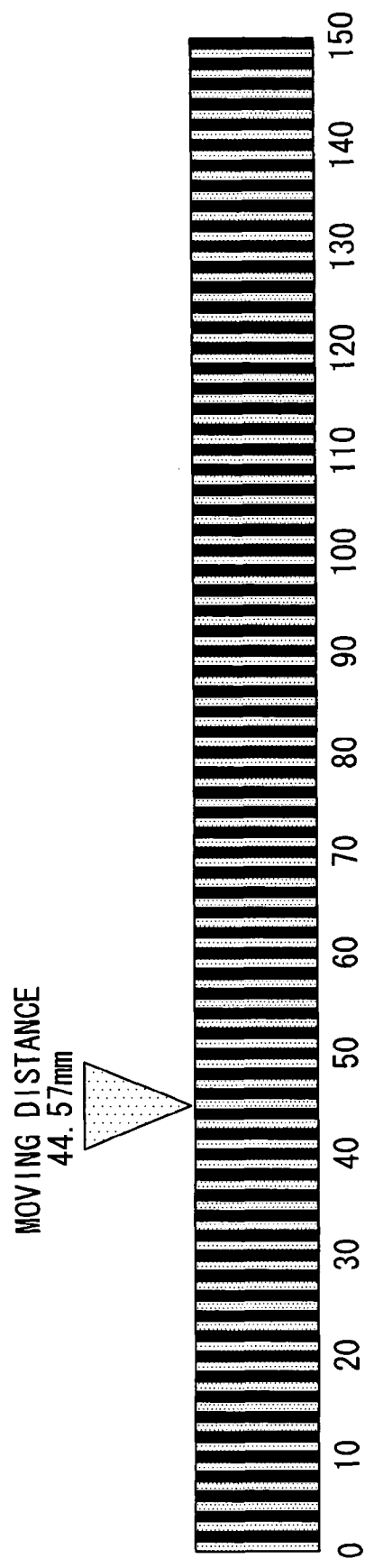
FIG. 15 is a view illustrating an exemplary display of a moving distance of the insertion part.

In the above-described embodiment, the case that the widths of the marks that have spaces between them in the insertion direction are varied is described. However, as shown in FIG. 14, banded marks that have an equal width may be employed. Then, a moving distance may be detected by counting the number of the marks. On the image display part, as shown in FIG. 15, a moving distance of the insertion part may be displayed.

Figure 16:
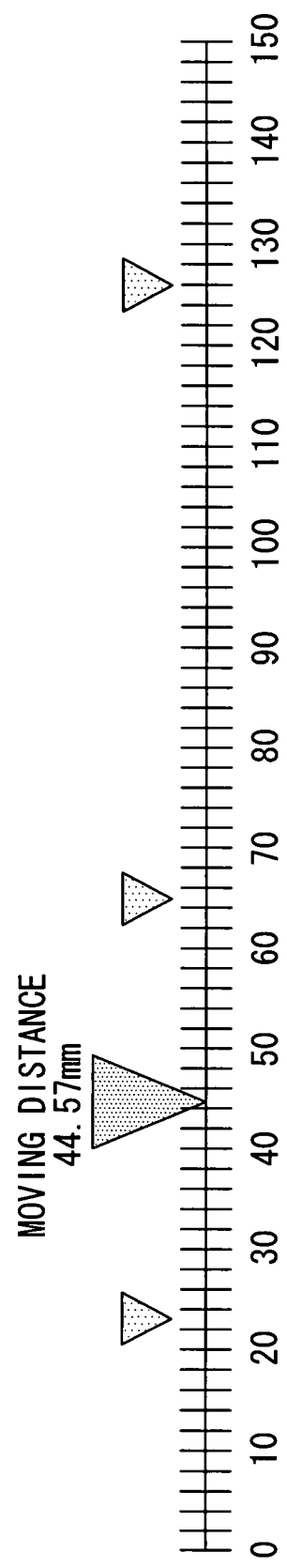
FIG. 16 is a view illustrating an exemplary display of a high-luminance part together with a moving distance of the insertion part.

As shown in FIG. 16, together with an indication of a moving distance of the insertion part, parts that indicate high total values of luminance may be displayed. Thus, at the parts that have the high luminance values and high possibilities of disease, the insertion part may be slowly moved to precisely observe the parts, and at the other parts, the insertion part may be quickly moved to increase the observation efficiency.

What is claimed is:

1. An endoscope system comprising:
   a light source for emitting an illumination light to illuminate an living organism;
   an insertion part to be inserted into the living organism for guiding the illumination light emitted from the light source and a light returned from the living organism;
   a deflection optical system being provided at a tip of the insertion part for outwardly directing the illumination light guided through the insertion part in a direction of a radius of the insertion part and for introducing a light inwardly returned from the living organism in the direction of the radius of the insertion part into the insertion part;
   an image capturing part for capturing the returned light guided through the insertion part and for forming a strip-shaped image corresponding to the captured returned light;
   an insertion speed detection part for detecting an insertion speed of the insertion part;
   a frame rate adjustment part for adjusting a frame rate for the image capturing of the image capturing part based on the insertion speed detected by the insertion speed detection part;
   a control part for correcting an exposure time of the image capturing part to be reduced and a sensitivity of the image capturing part to be increased in a case where the detected insertion speed is increased, and correcting the exposure time to be increased and the sensitivity to be decreased in a case where the detected insertion speed is decreased, the sensitivity of the image capturing of the image capturing part being adjusted corresponding to the exposure time of the image capturing part so that an intensity of the strip-shaped image formed by the image capturing part is prevented from being varied;
   an image forming part for arranging the strip-shaped images formed by the image capturing part at a pitch based on the insertion speed to form a two-dimensional image of the inside of the living organism; and
   a display part for displaying the two-dimensional image formed by the image forming part.

2. The endoscope system according to claim 1, wherein the insertion speed detection part comprises:
   a mark being provided on an outer surface of the insertion part along an insertion direction;
   a mark detection part for detecting the mark; and
   a speed calculation part for calculating an insertion speed based on the detected mark.

3. The endoscope system according to claim 1, wherein the returned light comprises at least one of a fluorescence and a white light.

4. The endoscope system according to claim 1, wherein the deflection optical system comprises a conical mirror.

5. An endoscope system comprising:
   an illumination light generation means for generating an illumination light to illuminate an living organism;
   an insertion means for being inserted into the living organism and for guiding the illumination light emitted from the light source and a light returned from the living organism;
   a deflection optical means being provided at a tip of the insertion part for outwardly directing the illumination light guided through the insertion part in a direction of a radius of the insertion part and for introducing a light inwardly returned from the living organism in the direction of the radius of the insertion part into the insertion part;
   an image capturing means for capturing the returned light guided through the insertion part and for forming a strip-shaped image corresponding to the captured returned light;
   an insertion speed detection means for detecting an insertion speed of the insertion part;
   a frame rate adjustment means for adjusting a frame rate for the image capturing of the image capturing part based on the insertion speed detected by the insertion speed detection part;

a control means for correcting an exposure time of the image capturing means to be reduced and a sensitivity of the image capturing means to be increased in a case where the detected insertion speed is increased, and correcting the exposure time to be increased and the sensitivity to be decreased in a case where the detected insertion speed is decreased, the sensitivity of the image capturing means being adjusted corresponding to the exposure time of the image capturing means so that an intensity of the strip-shaped image formed by the image capturing means is prevented from being varied;

an image forming means for arranging the strip-shaped images formed by the image capturing means at a pitch based on the insertion speed to form a two-dimensional image of the inside of the living organism; and a display means for displaying the two-dimensional image formed by the image forming means.

6. An endoscopic observation method in which an illumination light is outwardly emitted from a tip of an insertion part to be inserted into a living organism in a radius direction at each position in an insertion direction, a light returned from the living organism is captured to acquire strip-shaped images, the acquired strip-shaped images are arranged to form a two-dimensional image of the inside of the living organism, and the formed two-dimensional image is displayed, the method comprising:

detecting an insertion speed of the insertion part;

adjusting a frame rate for acquiring the strip-shaped images based on the detected insertion speed;

correcting an exposure time for acquiring the strip-shaped images to be reduced and a sensitivity for acquiring the strip-shaped images to be increased in a case where the detected insertion speed is increased; and correcting the exposure time to be increased and the sensitivity to be decreased in a case where the detected insertion speed is decreased, wherein the sensitivity being adjusted corresponding to the exposure time so that an intensity of the acquired strip-shaped image is prevented from being varied.

* * * * *